United States Patent
Ono et al.

(10) Patent No.: US 10,081,630 B2
(45) Date of Patent: Sep. 25, 2018

(54) RADIOACTIVE HALOGEN-LABELED PYRIDO [1,2-A] BENZIMIDAZOLE DERIVATIVE COMPOUND

(71) Applicants: KYOTO UNIVERSITY, Kyoto-shi, Kyoto (JP); NIHON MEDI-PHYSICS CO., LTD., Koto-ku, Tokyo (JP)

(72) Inventors: Masahiro Ono, Kyoto (JP); Hideo Saji, Kyoto (JP); Masafumi Ihara, Kyoto (JP); Hiroki Matsumoto, Tokyo (JP); Ikuya Seki, Tokyo (JP)

(73) Assignees: KYOTO UNIVERSITY, Kyoto-Shi, Kyoto (JP); NIHON MEDI-PHYSICS CO., LTD., Koto-Ku, Tokyo (JP)

( * ) Notice: Subject to any disclaimer, the term of this patent is extended or adjusted under 35 U.S.C. 154(b) by 0 days.

(21) Appl. No.: 15/543,849

(22) PCT Filed: Feb. 24, 2016

(86) PCT No.: PCT/JP2016/055357
§ 371 (c)(1),
(2) Date: Jul. 14, 2017

(87) PCT Pub. No.: WO2017/029820
PCT Pub. Date: Feb. 23, 2017

(65) Prior Publication Data
US 2017/0362226 A1    Dec. 21, 2017

(30) Foreign Application Priority Data

Aug. 19, 2015   (JP) .................................. 2015-161472

(51) Int. Cl.
| C07B 59/00 | (2006.01) |
| C07B 63/04 | (2006.01) |
| C07D 471/04 | (2006.01) |
| A61K 51/04 | (2006.01) |

(52) U.S. Cl.
CPC ........ C07D 471/04 (2013.01); A61K 51/0455 (2013.01); C07B 59/002 (2013.01); C07B 2200/05 (2013.01)

(58) Field of Classification Search
CPC .............. C07D 471/04; A61K 51/0455; C07B 2200/05

USPC .......................................................... 546/86
See application file for complete search history.

(56) References Cited

U.S. PATENT DOCUMENTS

| 2010/0239496 A1 | 9/2010 | Gangadharmath et al. |
| 2011/0182812 A1* | 7/2011 | Szardenings .......... A61K 51/04 424/1.89 |
| 2012/0302755 A1 | 11/2012 | Szardenings et al. |
| 2012/0330024 A1 | 12/2012 | Saji et al. |

FOREIGN PATENT DOCUMENTS

| JP | 2012-521988 A | 9/2012 |
| JP | 2013-522365 A | 6/2013 |
| JP | 2013-237655 A | 11/2013 |
| JP | 2015-089879 A | 5/2015 |
| JP | 2015-517572 A | 6/2015 |
| WO | WO 2011/108236 A1 | 9/2011 |
| WO | WO 2013/176698 A1 | 11/2013 |

OTHER PUBLICATIONS

International Search Report (PCT/ISA/210) dated Apr. 19, 2016, by the Japanese Patent Office as the International Searching Authority for International Application No. PCT/JP2016/055357.
Written Opinion (PCT/ISA/237) dated Apr. 19, 2016, by the Japanese Patent Office as the International Searching Authority for International Application No. PCT/JP2016/055357.
International Search Report (PCT/ISA/210) dated on Apr. 19, 2016, by the Japanese Patent Office as the International Searching Authority for International Application No. PCT/JP2016/055356.
Written Opinion (PCT/ISA/237) dated Apr. 19, 2016, by the Japanese Patent Office as the International Searching Authority for International Application No. PCT/JP2016/055356.
"DVD Abstracts of the 135 Annual Meeting of the Pharmaceutical Society of Japan in Kobe" with Certificates for receiving the application of the provisions of the exception of the novelty of the loss of the invention 1. (7 pages).

* cited by examiner

*Primary Examiner* — Rita J Desai
(74) *Attorney, Agent, or Firm* — Buchanan, Ingersoll & Rooney PC

(57) ABSTRACT

The present invention relates to a radioactive halogen-labeled pyrido[1,2-a]benzimidazole derivative compound represented by a specific general formula or a salt thereof, or a radiopharmaceutical comprising the same.

8 Claims, 2 Drawing Sheets

RADIOACTIVE HALOGEN-LABELED PYRIDO [1,2-A] BENZIMIDAZOLE DERIVATIVE COMPOUND

TECHNICAL FIELD

The present invention relates to a radioactive halogen-labeled pyrido[1,2-a]benzimidazole derivative compound or a salt thereof, and a radiopharmaceutical comprising the same.

RELATED ART

Accumulation of senile plaque (SP) composed mainly of amyloid β protein (Aβ) and neurofibrillary tangle (NFT) composed mainly of tau protein is found in the brain with Alzheimer's disease (AD). Since the accumulation of NFT exhibits high correlation with clinical symptoms, as compared with SP, development of radioactive molecule imaging probes for nuclear medicine diagnosis targeting the tau protein has received attention recently.

For example, Patent Document 1 describes radioactive iodine-labeled compounds comprising rhodanine and thiohydantoin derivatives having affinity for the tau protein.

Also, Patent Documents 2 to 4 describe compounds having binding activity against both of the Aβ and the tau protein. Specifically, Patent Document 2 describes a radioactive iodine-labeled compound having styrylbenzimidazole as a nucleus, Patent Document 3 describes benzimidazolepyrimidines, and Patent Document 4 describes a radioactive iodine-labeled compound having styrylbenzothiazole as a nucleus.

RELATED DOCUMENTS

Patent Documents

Patent Document 1: International Publication No. WO 2011/108236
Patent Document 2: Japanese Patent Laid-Open (Kokai) No. 2013-237655
Patent Document 3: Japanese Patent Laid-Open (Kohyo) No. 2013-522365
Patent Document 4: Japanese Patent Laid-Open (Kokai) No. 2015-89879

SUMMARY

However, the compounds described in Patent Documents 1 to 4 still need to be improved for in vivo imaging agents selective for the tau protein.

The present invention has been made in light of these circumstances, and aims to provide a novel tau imaging agent capable of selectively imaging a tau protein in living body by a nuclear medicine approach noninvasively.

The present inventors have completed the present invention by newly finding that a radioactive halogen-labeled pyrido[1,2-a]benzimidazole derivative compound having a pyrido[1,2-a]benzimidazole skeleton into which a substituent smaller than a phenyl group is introduced suppresses the nonspecific accumulation to the white matter while maintaining selective binding activity against the tau protein.

One aspect of the present invention provides a radioactive halogen-labeled compound represented by the following general formula (1) or a salt thereof:

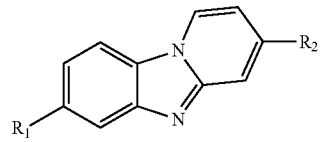

In the general formula (1), one of $R_1$ and $R_2$ is a radioactive halogen atom, and the other is an alkyl group having 1 to 4 carbon atoms, an alkoxy group having 1 to 4 carbon atoms, an amino group, an alkylamino group having 1 to 4 carbon atoms, or a dialkylamino group having 2 to 4 carbon atoms.

Another aspect of the present invention provides a radiopharmaceutical comprising the aforementioned radioactive halogen-labeled compound or a salt thereof.

Still another aspect of the present invention provides a diagnostic agent for Alzheimer's disease comprising the aforementioned radioactive halogen-labeled compound or a salt thereof.

Still another aspect of the present invention provides a compound represented by the following general formula (2) or a salt thereof:

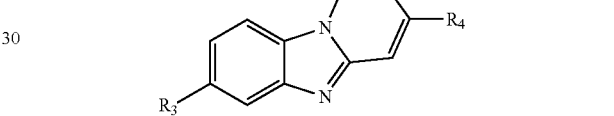

In the general formula (2), one of $R_3$ and $R_4$ is a halogen atom, a trialkylstannyl group, or a trialkylsilyl group, and the other is an alkyl group having 1 to 4 carbon atoms, an alkoxy group having 1 to 4 carbon atoms, an amino group, an alkylamino group having 1 to 4 carbon atoms, or a dialkylamino group having 2 to 4 carbon atoms.

Still another aspect of the present invention provides a method for producing a radioactive halogen-labeled compound represented by the general formula (1) or a salt thereof from a compound represented by the general formula (2) or a salt thereof by radioactive halogenation reaction.

The present invention can provide a novel tau imaging agent which is capable of selectively imaging a tau protein in living body by a nuclear medicine approach.

The object mentioned above and other objects, features, and advantages will become further apparent from the following preferred embodiments and the accompanying drawings shown below.

BRIEF DESCRIPTION OF DRAWINGS

FIG. 5A shows results of immunostaining with an antibody against tau using a brain tissue section of the frontal lobe. FIG. 5B shows results of immunostaining with an antibody against Aβ using a brain tissue section of the frontal lobe. FIG. 5C shows results of immunostaining with an antibody against tau using a brain tissue section of the temporal lobe. FIG. 5D shows results of immunostaining with an antibody against Aβ using a brain tissue section of the temporal lobe. FIG. 5E shows results of evaluating the binding affinity of [$^{125}$I]BIP-NMe$_2$ using a brain tissue section of the frontal lobe. FIG. 5F shows results of evaluating the binding capability of [$^{125}$I]BIP-NMe$_2$ using a brain tissue section of the temporal lobe. FIG. 5G shows results of evaluating the binding capability of [$^{125}$I]BIP-OMe using a brain tissue section of the frontal lobe. FIG. 5H shows results of evaluating the binding capability of [$^{125}$I]BIP-OMe using a brain tissue section of the temporal lobe. FIG. 5I shows results of evaluating the binding capability of [$^{125}$I]BIP-Me using a brain tissue section of the frontal lobe. FIG. 5J shows results of evaluating the binding capability of [$^{125}$I]BIP-Me using a brain tissue section of the temporal lobe.

DESCRIPTION OF EMBODIMENTS

Figure 1:
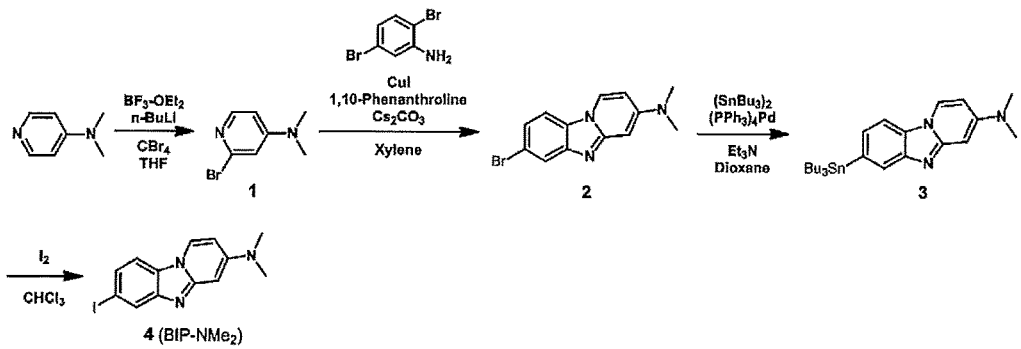
FIG. 1 is a diagram showing a synthesis example of 7-iodo-3-dimethylaminopyrido[1,2-a]benzimidazole (BIP-NMe$_2$) and a labeling precursor compound for the radioactive iodine-labeled BIP-NMe$_2$.

In the present invention, the "radioactive halogen atom" is at least one selected from radioisotopes of fluorine, chlorine, bromine, and iodine. Preferably, $^{18}$F, $^{34m}$Cl, $^{76}$Br, $^{123}$I, $^{124}$I, $^{125}$I, or $^{131}$I can be used.

In the present invention, the "radioactive iodine atom" is not particularly limited as long as it is a radioisotope of iodine, but is preferably a radioactive species used in nuclear medicine diagnostic imaging such as positron emission tomography (PET) and single photon emission computed tomography (SPECT), and more preferably, $^{123}$I, $^{124}$I, $^{125}$I, or $^{131}$I. $^{123}$I is furthermore preferred for SPECT.

In the present invention, the "alkyl group" may be linear or branched and is an alkyl group having 1 to 4 carbon atoms (a methyl group, an ethyl group, a n-propyl group, an isopropyl group, a n-butyl group, an isobutyl group, or a tert-butyl group), preferably an alkyl group having 1 to 3 carbon atoms (a methyl group, an ethyl group, a n-propyl group, or an isopropyl group), more preferably an alkyl group having 1 or 2 carbon atoms (a methyl group or an ethyl group).

In the present invention, the "alkoxy group" is an alkyl ether group in other words wherein the "alkyl" has the same meaning as the "alkyl group" mentioned above.

In the present invention, the "alkylamino group" is a group (NHR$_a$ (R$_a$ is an alkyl group)) resulting from substitution of one hydrogen atom of an amino group (NH$_2$) with an alkyl group.

In the present invention, the "dialkylamino group" is a group (NR$_a$R$_b$ (R$_a$ and R$_b$ are each independently an alkyl group)) resulting from substitution of each of two hydrogen atoms of an amino group with an alkyl group, and has 2 to 4 carbon atoms.

The "alkyl group" (R$_a$ and R$_b$) in the "alkylamino group" and the "dialkylamino group" also has the same meaning as the "alkyl group" mentioned above.

The radioactive halogen-labeled compound represented by the general formula (1) may form a salt. Examples of the salt include acid addition salts, for example, inorganic acid salts (e.g., hydrochloride, sulfate, hydrobromide, and phosphate) and organic acid salts (e.g., acetate, trifluoroacetate, succinate, maleate, fumarate, propionate, citrate, tartrate, lactate, oxalate, methanesulfonate, and p-toluenesulfonate). The compound represented by the general formula (1) or the salt thereof may be a hydrate.

Preferred examples of the radioactive halogen-labeled compound according to the present invention include a radioactive halogen-labeled compound of the general formula (1) wherein R$_1$ is a radioactive halogen atom, and R$_2$ is an alkyl group having 1 to 4 carbon atoms, an alkoxy group having 1 to 4 carbon atoms, or a dialkylamino group having 2 to 4 carbon atoms.

Specific examples of the radioactive halogen-labeled compound according to the present invention include the following radioactive iodine-labeled compounds:

radioactive iodine-labeled 7-iodo-3-aminopyrido[1,2-a]benzimidazole (a radioactive iodine-labeled compound of the general formula (1) wherein R$_1$ is a radioactive iodine atom, and R$_2$ is an amino group), radioactive iodine-labeled 7-iodo-3-methylaminopyrido[1,2-a]benzimidazole (a radioactive iodine-labeled compound of the general formula (1) wherein R$_1$ is a radioactive iodine atom, and R$_2$ is a methylamino group), radioactive iodine-labeled 7-iodo-3-dimethylaminopyrido[1,2-a]benzimidazole (a radioactive iodine-labeled compound of the general formula (1) wherein R$_1$ is a radioactive iodine atom, and R$_2$ is a dimethylamino group), radioactive iodine-labeled 7-iodo-3-methoxypyrido[1,2-a]benzimidazole (a radioactive iodine-labeled compound of the general formula (1) wherein R$_1$ is a radioactive iodine atom, and R$_2$ is a methoxy group), radioactive iodine-labeled 7-iodo-3-methylbenzo[4,5]imidazo[1,2-a]pyridine (a radioactive iodine-labeled compound of the general formula (1) wherein R$_1$ is a radioactive iodine atom, and R$_2$ is a methyl group), radioactive iodine-labeled 7-amino-3-iodopyrido[1,2-a]benzimidazole (a radioactive iodine-labeled compound of the general formula (1) wherein R$_1$ is an amino group, and R$_2$ is a radioactive iodine atom), radioactive iodine-labeled 7-methylamino-3-iodopyrido[1,2-a]benzimidazole (a radioactive iodine-labeled compound of the general formula (1) wherein R$_1$ is a methylamino group, and R$_2$ is a radioactive iodine atom)

radioactive iodine-labeled 7-dimethylamino-3-iodopyrido[1,2-a]benzimidazole (a radioactive iodine-labeled compound of the general formula (1) wherein R$_1$ is a dimethylamino group, and R$_2$ is a radioactive iodine atom), radioactive iodine-labeled 7-methoxy-3-iodopyrido[1,2-a]benzimidazole (a radioactive iodine-labeled compound of the general formula (1) wherein R$_1$ is a methoxy group, and R$_2$ is a radioactive iodine atom), and radioactive iodine-labeled 7-methyl-3-iodobenzo[4,5]imidazo[1,2-a]pyridine (a radioactive iodine-labeled compound of the general formula (1) wherein R$_1$ is a methyl group, and R$_2$ is a radioactive iodine atom).

Subsequently, a method for producing the radioactive halogen-labeled compound represented by the general formula (1) or the salt thereof will be described. The radioactive halogen-labeled compound represented by the general formula (1) or the salt thereof can be obtained by carrying out a radioactive halogenation reaction using a compound represented by the general formula (2) or a salt thereof.

In the general formula (2), the "halogen atom" is at least one selected from a fluorine atom, a chlorine atom, a bromine atom, and an iodine atom.

The trialkylstannyl group in the general formula (2) includes tri(C1-C6 alkyl)stannyl groups, and more preferably a tributylstannyl group. The trialkylsilyl group includes tri(C1-C6 alkyl)silyl groups, and more preferably a trimethylsilyl group.

The compound represented by the general formula (2) may form a salt. The same as the salt that may be formed by the radioactive halogen-labeled compound represented by the general formula (1) can be adopted as the salt.

The compound represented by the general formula (2) wherein $R_3$ is a halogen atom, a trialkylstannyl group, or a trialkylsilyl group, and $R_4$ is an alkyl group having 1 to 4 carbon atoms, an alkoxy group having 1 to 4 carbon atoms, an amino group, an alkylamino group having 1 to 4 carbon atoms, or a dialkylamino group having 2 to 4 carbon atoms can be prepared by a method, for example, according to scheme 1.

Scheme 1

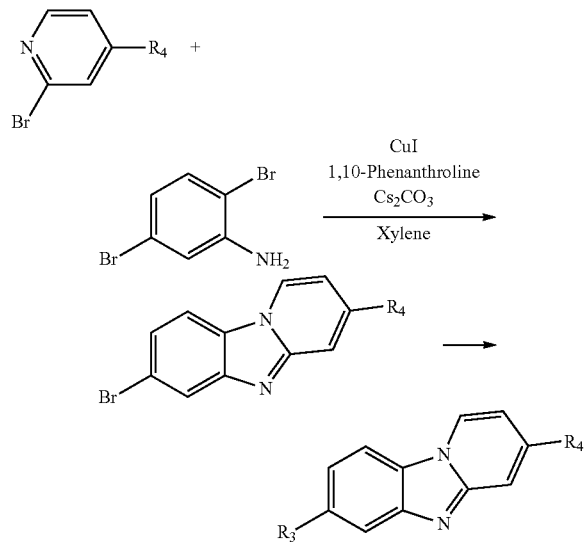

Specifically, dibromoaniline is allowed to act on a 2-bromopyridine derivative carrying, at position 4, a substituent corresponding to $R_4$ of the general formula (2) in the presence of copper(I) iodide, cesium carbonate, and 1,10-phenanthroline in xylene. Subsequently, the bromo group can be replaced with a substituent corresponding to $R_3$ of the general formula (2).

Also, the compound represented by the general formula (2) wherein $R_3$ is an alkyl group having 1 to 4 carbon atoms, an alkoxy group having 1 to 4 carbon atoms, an amino group, an alkylamino group having 1 to 4 carbon atoms, or a dialkylamino group having 2 to 4 carbon atoms, and $R_4$ is a halogen atom, a trialkylstannyl group, or a trialkylsilyl group can be prepared by a method, for example, according to scheme 2.

Scheme 2

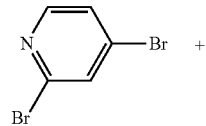

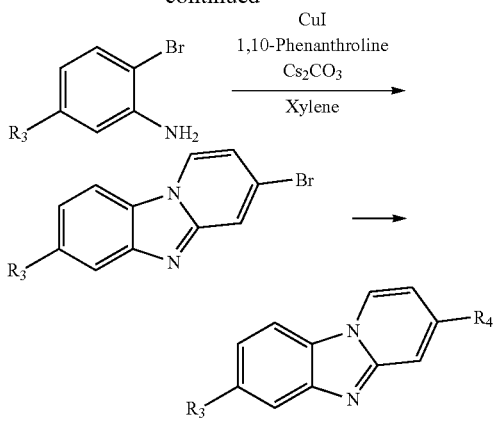

Specifically, 2,4-dibromopyridine is allowed to act on o-bromoaniline carrying, at meta position, a substituent corresponding to $R_3$ of the general formula (2) in the presence of copper(I) iodide, cesium carbonate, and 1,10-phenanthroline in xylene. Subsequently, the bromo group can be replaced with a substituent corresponding to $R_4$ of the general formula (2).

In order to synthesize the compound of the general formula (2) wherein either $R_3$ or $R_4$ is an amino group or an alkylamino group having 1 to 4 carbon atoms in the schemes 1 and 2, the amino group or the alkylamino group may be protected before formation of the pyrido[1,2-a]benzimidazole skeleton, and deprotected after the formation of the pyrido[1,2-a]benzimidazole skeleton or after radioactive halogenation reaction mentioned later. The selection of a protective group, introduction conditions of the protective group, and deprotection conditions can follow the description of Greene's Protective Groups in Organic Synthesis (John Wiley & Sons Inc.; 5th Revised edition).

The radioactive halogenation reaction can be performed using a radioactive halogen prepared as an electrophile and can be performed using, for example, a radioactive halogen molecule or a radioactive acetyl hypohalide. Examples of the radioactive halogen molecule include a radioactive fluorine molecule, a radioactive chlorine molecule, a radioactive bromine molecule, and a radioactive iodine molecule. Examples of the radioactive acetyl hypohalide include radioactive acetyl hypofluoride, radioactive acetyl hypochloride, radioactive acetyl hypobromide, and radioactive acetyl hypoiodide. Alternatively, a radioactive sodium halide or radioactive potassium halide may be reacted in the presence of an oxidizing agent under an acidic condition. For example, chloramine-T, hydrogen peroxide water, peracetic acid, or halogenated succinimide can be used as the oxidizing agent.

For example, the halogen atom, the trialkylstannyl group, or the trialkylsilyl group of $R_3$ or $R_4$ in the compound represented by the general formula (2) can be replaced with a radioactive iodine atom by radioactive iodination reaction using radioactive alkali metal iodide to obtain a radioactive iodine-labeled compound as a radioactive halogen-labeled compound represented by the general formula (1) wherein $R_1$ or $R_2$ is a radioactive iodine atom. It is preferred that the radioactive iodination reaction should be performed by reacting a radioactive alkali metal iodide and an oxidizing agent under an acidic condition. For example, a sodium compound of radioactive iodine or a potassium compound of radioactive iodine can be used as the radioactive alkali metal iodide. For example, chloramine-T, hydrogen peroxide water, peracetic acid, N-chlorosuccinimide, or N-bromosuccinimide can be used as the oxidizing agent. As one example, the radioactive iodination reaction can be performed by reacting a radioactive sodium iodide (e.g., [$^{123}$I] sodium iodide, [$^{124}$I]sodium iodide, [$^{125}$I]sodium iodide, or [$^{131}$I]sodium iodide) in the presence of an oxidizing agent such as hydrogen peroxide water under an acidic condition involving hydrochloric acid or the like, to obtain a radioactive iodine-labeled compound of the general formula (1) wherein $R_1$ or $R_2$ is a radioactive iodine atom.

In the case of using the obtained radioactive halogen-labeled compound of the general formula (1) as a radiopharmaceutical, it is desirable to remove unreacted radioactive iodide ions and insoluble impurities by purification using a membrane filter, a column packed with various packing materials, HPLC, or the like.

The radiopharmaceutical according to the present invention can be defined as a formulation comprising the radioactive halogen-labeled compound represented by the general formula (1) or the salt thereof in a form suitable for administration into a living body. This radiopharmaceutical can be prepared as a liquid in which the obtained radioactive halogen-labeled compound of the general formula (1) is mixed with water or saline adjusted, if desired, to appropriate pH, or a Ringer's solution or the like. In this case, it is preferred that the concentration of the present radioactive halogen-labeled compound should be equal to or lower than a concentration at which the stability of the present radioactive halogen-labeled compound mixed therein is obtained. The dosage form of the radiopharmaceutical according to the present invention is preferably an injection. The dose does not have to be particularly limited as long as it is a concentration sufficient for imaging the distribution of the administered compound.

The radiopharmaceutical of the present invention can be used as a diagnostic imaging agent for nuclear medicine examination and specifically, can be used for the purpose of a diagnostic imaging agent for positron emission tomography (PET) or a diagnostic imaging agent for single photon emission computed tomography (SPECT). For example, the radiopharmaceutical of the present invention can be used as a diagnostic imaging agent for positron emission tomography in the case of using a positron emitting radionuclide such as $^{18}$F, $^{76}$Br and $^{124}$I as the radioactive halogen atom, and can be used as a diagnostic imaging agent for single photon emission computed tomography in the case of using $^{123}$I as a radioactive halogen atom. The tau protein can be imaged on the image obtained by the nuclear medicine examination, and thus, for example, Alzheimer's disease can be noninvasively diagnosed.

EXAMPLES

Hereinafter, the present invention will be described further specifically with reference to Examples. However, the present invention is not intended to be limited by these contents.

Abbreviations used in the present Examples are defined as follows:
BIP-NMe$_2$: 7-iodo-3-dimethylaminopyrido[1,2-a]benzimidazole
BIP-OMe: 7-iodo-3-methoxypyrido[1,2-a]benzimidazole
BIP-Me: 7-iodo-3-methylbenzo[4,5]imidazo[1,2-a]pyridine
[$^{125}$I]BIP-NMe$_2$: 7-[$^{125}$I]iodo-3-dimethylaminopyrido[1,2-a]benzimidazole
[$^{125}$I]BIP-OMe: 7-[$^{125}$I]iodo-3-methoxypyrido[1,2-a]benzimidazole
[$^{125}$I]BIP-Me: 7-[$^{125}$I]iodo-3-methylbenzo[4,5]imidazo[1,2-a]pyridine In the present Examples, reagents purchased from Nacalai Tesque, Inc., Tokyo Chemical Industry Co., Ltd., Wako Pure Chemical Industries, Ltd., or Sigma-Aldrich Co. LLC were used. However, [$^{125}$I]sodium iodide was purchased from MP Biomedicals or PerkinElmer Japan Co., Ltd. and used. An automatically set preparative medium pressure liquid chromatograph system manufactured by Yamazen Corp. (EP-CLC-W-Prep 2XY; feeding pump (with a built-in mixer): No. 580D, detector (wavelength-fixed type): prep UV-254W, fraction collector: FR-260) was used as a preparative medium pressure liquid chromatography apparatus, which was equipped with HI-FLASH COLUMN (packing material: silica gel SiOH, pore size: 60 angstroms, particle size: 40 μm, column size: L or 2L) and INJECT COLUMN (packing material: silica gel SiOH, pore size: 60 angstroms, particle size: 40 μm, column size: M or L). For $^1$H-NMR, measurement was performed with tetramethylsilane as internal standards using an NMR apparatus JNM-AL400 manufactured by JEOL Ltd. All chemical shifts were indicated by ppm on a delta scale (δ), and the fine splitting of signals was indicated using abbreviations (s: singlet, d: doublet, dd: double doublet, m: multiplet). For electrospray ionization mass spectrometry (ESI-MS), measurement was performed using a high performance chromatograph mass spectrometer LCMS-2020 manufactured by Shimadzu Corp.

In the present Examples, "room temperature" means 25° C.

In the synthesis example of each compound, each step for the compound synthesis was repeated plural times according to need to secure an amount necessary for use as an intermediate or the like in other syntheses.

Wallac WIZARD 1480 manufactured by PerkinElmer Japan Co., Ltd. was used for measurement of radioactivity.

(Example 1) Synthesis of 7-tributylstannyl-3-dimethylaminopyrido[1,2-a]benzimidazole (a Labeling Precursor Compound for the Radioactive Iodine-Labeled BIP-NMe$_2$)

A labeling precursor compound (compound 3) for the radioactive iodine-labeled BIP-NMe$_2$ was obtained according to the scheme shown in FIG. 1.

Synthesis of 2-bromo-N,N-dimethylpyridin-4-amine (Compound 1)

Synthesis was performed on the basis of the method described in Org Biomol Chem, 11, 8073, 2013 to obtain compound 1 in an amount of 1.10 g (54.6%).

Synthesis of 7-bromo-3-dimethylaminopyrido[1,2-a]benzimidazole (Compound 2)

Compound 1 (1.10 g, 5.46 mmol) was dissolved in xylene (45.0 mL). To the solution, 2,5-dibromoaniline (1.37 g, 5.46 mmol), copper(I) iodide (208 mg, 1.09 mmol), cesium carbonate (5.34 g, 16.4 mmol), and 1,10-phenanthroline (393 mg, 2.18 mmol) were added, and the mixture was then heated to reflux for 72 hours with stirring. The reaction solution was brought back to room temperature, followed by extraction with chloroform (70 mL×2). The organic layer was washed with saturated saline and then dehydrated over anhydrous magnesium sulfate, and the solvent was distilled off under reduced pressure. The residue was subjected to silica gel column chromatography with chloroform/methanol (20/1) as an elution solvent to obtain compound 2 in an amount of 94.9 mg (6.00%).

$^1$H-NMR (400 MHz, deuterated chloroform) δ 8.16 (d, J=7.5 Hz, 1H), 7.86 (s, 1H), 7.56 (d, J=8.7 Hz, 1H), 7.30 (d, J=8.7 Hz, 1H), 6.60 (d, J=7.5 Hz, 1H), 6.55 (s, 1H), 3.14 (s, 6H).

MS (ESI) m/z 290.1 [MH$^+$].

Synthesis of 7-tributylstannyl-3-dimethylaminopyrido[1,2-a]benzimidazole (Compound 3)

Compound 2 (94.9 mg, 0.327 mmol) was dissolved in 1,4-dioxane (30.0 mL). To the solution, bis(tributyltin) (655 µL, 1.31 mmol), tetrakistriphenylphosphinepalladium (163 mg, 0.141 mmol), triethylamine (10.0 mL), and dimethylformamide (8 mL) were added, and the mixture was heated to reflux for 5.5 hours with stirring. The reaction solution was brought back to room temperature, followed by extraction with chloroform (90 mL×2). The organic layer was washed with saturated saline and then dehydrated over anhydrous magnesium sulfate, and the solvent was distilled off under reduced pressure. The residue was subjected to silica gel column chromatography with chloroform/methanol (15/1) as an elution solvent to obtain compound 3 in an amount of 18.0 mg (11.0%).

$^1$H-NMR (400 MHz, deuterated methanol) δ 8.41 (d, J=7.5 Hz, 1H), 7.81 (d, J=7.8 Hz, 1H), 7.66 (s, 1H), 7.24 (d, J=7.5 Hz, 1H), 6.65 (dd, J=7.8, 2.6 Hz, 1H), 6.32 (d, J=2.3 Hz, 1H), 3.06 (s, 6H), 1.56-1.63 (m, 6H), 1.32-1.41 (m, 6H), 1.10-1.14 (m, 6H), 0.88-0.92 (m, 9H). MS (ESI) m/z 502.4 [MH$^+$].

(Example 2) Synthesis of BIP-NMe$_2$ (Compound 4)

A non-radioactive compound (compound 4) of BIP-NMe$_2$ was obtained according to the scheme shown in FIG. 1.

Compound 3 (49.0 mg, 0.0979 mmol) synthesized according to the method shown in Example 1 was dissolved in chloroform (20.0 mL). To the solution, 2.50 mL of a solution of iodine in chloroform (50.0 mg/mL) was added, and the mixture was stirred at room temperature for 1.5 hours. The reaction was terminated with a saturated aqueous solution of sodium bisulfite, followed by extraction with chloroform (70.0 mL×2). The organic layer was washed with saturated saline and then dehydrated over anhydrous magnesium sulfate, and the solvent was distilled off under reduced pressure. The residue was subjected to silica gel column chromatography with chloroform/methanol (20/1) as an elution solvent to obtain BIP-NMe$_2$ in an amount of 5.50 mg (16.7%).

$^1$H-NMR (400 MHz, deuterated methanol) δ 8.75 (d, J=7.8 Hz, 1H), 7.94 (s, 1H), 7.85 (d, J=8.7 Hz, 1H), 7.72 (d, J=8.4 Hz, 1H), 7.08 (d, J=7.8 Hz, 1H), 6.56 (s, 1H), 3.25 (s, 6H).

HRMS (EI) m/z calcd for C$_{13}$H$_{12}$IN$_3$ (M$^+$) 337.0076, found 337.0074.

(Example 3) Synthesis of 7-tributylstannyl-3-methoxypyrido[1,2-a]benzimidazole (a Labeling Precursor Compound for the Radioactive Iodine-Labeled BIP-OMe)

Figure 2:
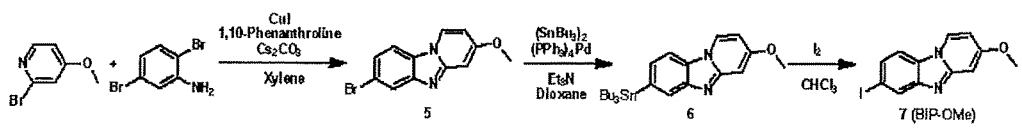
FIG. 2 is a diagram showing a synthesis example of 7-iodo-3-methoxypyrido[1,2-a]benzimidazole (BIP-OMe) and a labeling precursor compound for the radioactive iodine-labeled BIP-OMe.

A labeling precursor compound (compound 6) for the radioactive iodine-labeled BIP-OMe was obtained according to the scheme shown in FIG. 2.

Synthesis of 7-bromo-3-methoxypyrido[1,2-a]benzimidazole (Compound 5)

2-Bromo-4-methoxypyridine (1.23 mL, 10.0 mmol) was dissolved in xylene (50.0 mL). To the solution, 2,5-dibromoaniline (2.51 g, 10.0 mmol), copper(I) iodide (381 mg, 2.00 mmol), cesium carbonate (9.78 g, 30.0 mmol), and 1,10-phenanthroline (721 mg, 4.00 mmol) were added, and the mixture was then heated to reflux for 75 hours with stirring. The reaction solution was brought back to room temperature, followed by extraction with chloroform (120 mL×2). The organic layer was washed with saturated saline and then dehydrated over anhydrous magnesium sulfate, and the solvent was distilled off under reduced pressure. The residue was subjected to silica gel column chromatography with chloroform/methanol (49/1) as an elution solvent to obtain compound 5 in an amount of 223 mg (8.05%).

$^1$H-NMR (400 MHz, deuterated chloroform) δ 8.21 (d, J=7.5 Hz, 1H), 7.95 (d, J=1.7 Hz, 1H), 7.63 (d, J=8.7 Hz, 1H), 7.34 (dd, J=8.4, 1.7 Hz, 1H), 6.87 (d, J=2.3 Hz, 1H), 6.59 (dd, J=7.5, 2.6 Hz, 1H), 3.93 (s, 3H).

MS (ESI) m/z 277.1 [MH$^+$].

Synthesis of 7-tributylstannyl-3-methoxypyrido[1,2-a]benzimidazole (Compound 6)

Compound 5 (114 mg, 0.411 mmol) was dissolved in 1,4-dioxane (30.0 mL). To the solution, bis(tributyltin) (827 µL, 1.65 mmol), tetrakistriphenylphosphinepalladium (204 mg, 0.177 mmol), and triethylamine (15.0 mL) were added, and the mixture was heated to reflux for 2.5 hours with stirring. After the completion of reaction, the solvent was distilled off under reduced pressure. The residue was subjected to silica gel column chromatography with chloroform/methanol (49/1) as an elution solvent to obtain compound 6 in an amount of 47.9 mg (23.9%).

$^1$H-NMR (400 MHz, deuterated chloroform) δ 8.24 (d, J=7.5 Hz, 1H), 7.95 (s, 1H), 7.75 (d, J=7.5 Hz, 1H), 7.36 (d, J=7.8 Hz, 1H), 6.86 (d, J=2.3 Hz, 1H), 6.54 (dd, J=7.2, 2.3 Hz, 1H), 3.93 (s, 6H), 1.54-1.60 (m, 6H), 1.32-1.37 (m, 6H), 1.09-1.13 (m, 6H), 0.87-0.90 (m, 9H).

MS (ESI) m/z 489.3 [MH$^+$].

(Example 4) Synthesis of BIP-OMe (Compound 7)

A non-radioactive compound (compound 7) of BIP-OMe was obtained according to the scheme shown in FIG. 2.

Compound 6 (37.9 mg, 0.0778 mmol) synthesized according to the method shown in Example 3 was dissolved in chloroform (10.0 mL). To the solution, 1.00 mL of a solution of iodine in chloroform (50.0 mg/mL) was added, and the mixture was stirred at room temperature for 1.5 hours. The reaction was terminated with a saturated aqueous solution of sodium bisulfite, followed by extraction with chloroform (65.0 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (2/1) as an elution solvent to obtain BIP-OMe in an amount of 14.2 mg (56.3%).

$^1$H-NMR (400 MHz, deuterated chloroform) δ 8.20 (d, J=7.5 Hz, 1H), 8.17 (d, J=1.2 Hz, 1H), 7.51-7.57 (m, 2H), 6.86 (d, J=2.3 Hz, 1H), 6.56 (dd, J=7.5, 2.3 Hz, 1H), 3.93 (s, 6H).

HRMS (EI) m/z calcd for $C_{12}H_9IN_2O$ (M$^+$) 323.9760, found 323.9762.

(Example 5) Synthesis of 7-tributylstannyl-3-methylpyrido[1,2-a]benzimidazole (Compound 9) (a Labeling Precursor Compound for the Radioactive Iodine-Labeled BIP-Me)

Figure 3:
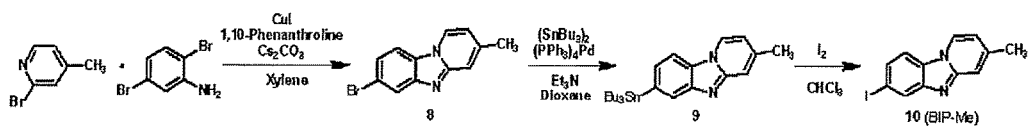
FIG. 3 is a diagram showing a synthesis example of 7-iodo-3-methylbenzo[4,5]imidazo[1,2-a]pyridine (BIP-Me) and a labeling precursor compound for the radioactive iodine-labeled BIP-Me.

A labeling precursor compound (compound 9) for the radioactive iodine-labeled BIP-Me was obtained according to the scheme shown in FIG. 3.

Synthesis of 7-bromo-3-methylpyrido[1,2-a]benzimidazole (Compound 8)

2-Bromo-4-methylpyridine (135 µL, 1.20 mmol) was dissolved in xylene (8.00 mL). To the solution, 2,5-dibromoaniline (251 mg, 1.00 mmol), copper(I) iodide (38.1 mg, 0.20 mmol), cesium carbonate (978 mg, 3.00 mmol), and 1,10-phenanthroline (72.1 mg, 0.40 mmol) were added, and the mixture was then heated to reflux for 57.5 hours with stirring. The reaction solution was brought back to room temperature, followed by extraction with chloroform (65 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (1/1) as an elution solvent to obtain compound 8 in an amount of 62.4 mg (23.9%).

$^1$H-NMR (400 MHz, deuterated chloroform) δ 8.28 (d, J=7.0 Hz, 1H), 8.02 (s, 1H), 7.70 (d, J=8.7 Hz, 1H), 7.40-7.43 (m, 2H), 6.72 (d, J=7.0 Hz, 1H), 2.48 (s, 3H).

MS (ESI) m/z 261.1 [MH$^+$].

Synthesis of 7-tributylstannyl-3-methylpyrido[1,2-a]benzimidazole (Compound 9)

Compound 8 (62.4 mg, 0.239 mmol) was dissolved in 1,4-dioxane (14.0 mL). To the solution, bis(tributyltin) (240 µL, 0.478 mmol), tetrakistriphenylphosphinepalladium (119 mg, 0.103 mmol), and triethylamine (7.00 mL) were added, and the mixture was heated to reflux for 2.5 hours with stirring. After the completion of reaction, the solvent was distilled off under reduced pressure. The residue was subjected to silica gel column chromatography with ethyl acetate/hexane (1/1) as an elution solvent to obtain compound 9 in an amount of 14.9 mg (13.2%).

$^1$H-NMR (400 MHz, deuterated chloroform) δ 8.31 (d, J=7.0 Hz, 1H), 8.02 (s, 1H), 7.82 (d, J=7.8 Hz, 1H), 7.38-7.42 (m, 2H), 6.66 (d, J=7.0 Hz, 1H), 2.46 (s, 3H), 1.53-1.61 (m, 6H), 1.32-1.39 (m, 6H), 1.10-1.14 (m, 6H), 0.86-0.91 (m, 9H).

MS (ESI) m/z 473.3 [MH$^+$].

(Example 6) Synthesis of BIP-Me (Compound 10)

A non-radioactive compound (compound 10) of BIP-Me was obtained according to the scheme shown in FIG. 3.

Compound 9 (12.9 mg, 0.0274 mmol) synthesized according to the method shown in Example 5 was dissolved in chloroform (13.0 mL). To the solution, 400 µL of a solution of iodine in chloroform (50.0 mg/mL) was added, and the mixture was stirred at room temperature for 1 hour. The reaction was terminated with a saturated aqueous solution of sodium bisulfite, followed by extraction with chloroform (40.0 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (1/1) as an elution solvent to obtain BIP-Me in an amount of 5.5 mg (65.2%).

$^1$H-NMR (400 MHz, deuterated chloroform) δ 8.29 (d, J=7.0 Hz, 1H), 8.24 (d, J=1.2 Hz, 1H), 7.60 (s, 2H), 7.43 (s, 1H), 6.72 (d, J=7.2 Hz, 1H), 2.49 (s, 3H).

HRMS (EI) m/z calcd for $C_{12}H_9IN_2$ (M$^+$) 307.9811, found 307.9808.

(Example 7) Synthesis of Radioactive Iodine-Labeled BIP Derivative Compound

Figure 4:
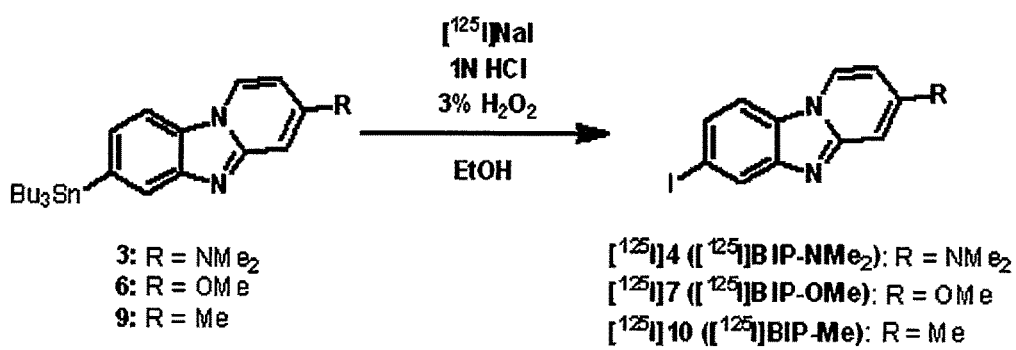
FIG. 4 is a diagram showing a $^{125}$I-labeling example of radioactive iodine-labeled pyrido[1,2-a]benzimidazole derivative compounds.

[$^{125}$I]BIP-NMe$_2$, [$^{125}$I]BIP-OMe, and [$^{125}$I]BIP-Me were obtained according to the scheme shown in FIG. 4. Specifically, compound 3 synthesized according to the method shown in Example 1, compound 6 synthesized according to the method shown in Example 3, and compound 9 synthesized according to the method shown in Example 5 were each used and labeled with radioactive iodine by tin-iodine exchange reaction. More specifically, [$^{125}$I]sodium iodide (3.7 to 7.4 MBq, specific radioactivity: 81.4 TBq/mmol) was added to 1 mol/L hydrochloric acid (100 µL) and 3% hydrogen peroxide water (100 µL), and a solution of each of compounds 3, 6, and 9 in ethanol (1.00 mg/mL or 2.00 mg/mL, 200 µL) was added thereto. After reaction at room temperature for 40 minutes, the reaction was terminated by addition of a saturated aqueous solution of sodium bisulfite (200 µL) as a reducing agent. The reaction solution was neutralized by addition of a saturated aqueous solution of sodium bicarbonate (200 µL), followed by extraction of the compound of interest with ethyl acetate. The extract was dehydrated through a column packed with anhydrous sodium sulfate, and the solvent was then distilled off. The obtained radioactive iodine-labeled compounds 4, 7, and 10 were purified using reverse phase high performance liquid chromatography (HPLC) with the corresponding non-radioactive compounds 4, 7, and 10 as standards, followed by extraction of the compound of interest with ethyl acetate. The extract was dehydrated through a column packed with anhydrous sodium sulfate, and the solvent was then distilled off.

Each compound of [$^{125}$I]BIP-NMe$_2$, [$^{125}$I]BIP-OMe, and [$^{125}$I]BIP-Me was obtained at a radiochemical yield of 39 to 49% and a radiochemical purity of 99% or higher.

LC-20AD or LC-20AT manufactured by Shimadzu Corp. was used for HPLC, and an ultraviolet spectrum detector SPD-20A and a scintillation survey meter TCS-172 manufactured by Hitachi Aloka Medical, Ltd. or a radiation detector US-000T for HPLC manufactured by Universal Giken Co., Ltd. were used as detectors. COSMOSIL 5C18-AR-II 4.6 mm I.D.×150 mm manufactured by Nacalai Tesque, Inc. was used as a column for reverse phase HPLC. A mobile phase and retention time of reverse phase HPLC are shown in Table 1.

TABLE 1

| Compound | Mobile phase (volume ratio) | Retention time (min) |
|---|---|---|
| 4(BIP-NMe$_2$) | Acetonitrile/water = 25/75 (0.1% trifluoroacetic acid) | 11.4 |
| 7(BIP-OMe) | Acetonitrile/water = 4/6 | 18.6 |
| 10(BIP-Me) | Acetonitrile/water = 2/8 (0.1% trifluoroacetic acid) | 9.24 |

(Evaluation 1) In Vitro Autoradiography Using Autopsied Brain Tissue of Alzheimer's Disease Patient
(1) In Vitro Autoradiography Autopsied brain tissue sections of an Alzheimer's disease (AD) patient (76 years old, male, sections from a frontal lobe site and a temporal lobe site, 6 µm) were used, which were provided from Graduate School of Medicine, Kyoto University and National Cerebral and Cardiovascular Center Hospital. Deparaffinization treatment was performed by washing with xylene (15 min×2), ethanol (1 min×2), a 90 vol % aqueous ethanol solution (1 min×1), an 80 vol % aqueous ethanol solution (1 min×1), a 70 vol % aqueous ethanol solution (1 min×1), and purified water (2.5 min×2). A 10 vol % aqueous ethanol solution of each radioactive iodine-labeled BIP derivative compound (370 kBq/mL) obtained by the method shown in Example 7 was added thereto, and the tissue sections were incubated at room temperature for 2 hours. The tissue sections were washed with a 50 vol % aqueous ethanol solution (1 hr×1), then exposed to an imaging plate (BAS-SR2025 manufactured by Fujifilm Corp.), and analyzed using a bioimaging analyzer (bioimaging analyzer BAS-5000 manufactured by Fujifilm Corp.). Multi Gauge manufactured by Fujifilm Corp. was used in quantitative analysis.

Figure 5:
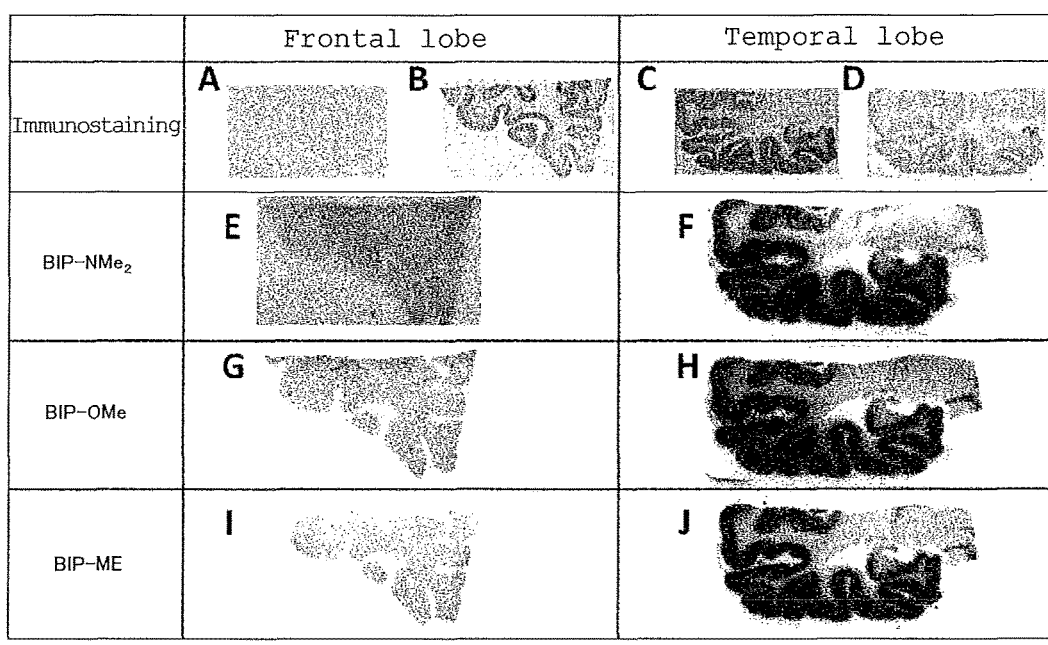
FIG. 5A-5J is a diagram showing results of immunostaining and in vitro autoradiography using an autopsied brain tissue of an Alzheimer's disease patient.

The results are shown in FIG. 5. FIGS. 5E and 5F show the results obtained using [$^{125}$I]BIP-NMe$_2$. FIGS. 5G and 5H show the results obtained using [$^{125}$I]BIP-OMe. FIGS. 5I and 5J show the results obtained using [$^{125}$I]BIP-Me. FIGS. 5E, 5G, and 5I show the results obtained using the brain tissue section of the frontal lobe. FIGS. 5F, 5H, and 5J show the results obtained using the brain tissue section of the temporal lobe. As shown in FIGS. 5E, 5G, and 5I, none of [$^{125}$I]BIP-NMe$_2$, [$^{125}$I]BIP-OMe, and [$^{125}$I]BIP-Me exhibited radioactivity accumulation in the brain tissue section of the frontal lobe. As shown in FIGS. 5F, 5H, and 5J, they exhibited radioactivity accumulation in only the brain tissue section of the temporal lobe, indicating that they maintain binding selectivity for tau accumulated in the brain with AD. These compounds exhibited low nonspecific binding to the brain white matter, and, as a result, provided images with high contrast between the gray matter and the white matter.

(2) Immunostaining Using Autopsied Brain Tissue Section of AD Patient

Tau and Aβ were immunostained using sections adjacent to the autopsied AD brain tissue sections used in autoradiography. An anti-phosphorylated tau monoclonal antibody (AT8, manufactured by Thermo Fisher Scientific Inc.) was used as a primary antibody in the immunostaining of tau, and an anti-Aβ$_{1-42}$ monoclonal antibody (BC05, manufactured by Wako Pure Chemical Industries, Ltd.) was used as a primary antibody in the immunostaining of Aβ. Deparaffinization treatment was performed by washing with xylene (15 min×2), ethanol (1 min×2), a 90 vol % aqueous ethanol solution (1 min×1), an 80 vol % aqueous ethanol solution (1 min×1), a 70 vol % aqueous ethanol solution (1 min×1), and purified water (2.5 min×2). The antigens were retrieved by autoclaving (15 min) in a 0.01 mol/L citrate buffer solution (pH 6.0) and formic acid treatment (5 min). The tissue sections were washed with running water (5 min) and then washed with PBS-Tween 20 (2 min×1). The tissue sections were reacted with primary antibody solutions at room temperature for 1 hour and then washed with PBS-Tween 20 (5 min×3). The tissue sections were reacted with Histofine Simple Stain MAX-PO (MULTI) (manufactured by Nichirei Biosciences Inc.) at room temperature for 30 minutes and then washed with PBS-Tween 20 (3 min×3) and TBS (5 min×1). Finally, the tissue sections were reacted with a DAB solution at room temperature for 1 minute. The tissue sections were washed with distilled water (1 min×1) to terminate the reaction. The brain tissue sections were mounted on slides and then observed under a microscope (BZ-9000 manufactured by Keyence Corporation).

The results are shown in FIG. 5. FIGS. 5A and 5B show the results obtained using the brain tissue section of the frontal lobe. FIGS. 5C and 5D show the results obtained using the brain tissue section of the temporal lobe. FIGS. 5A and 5C show the results of immunostaining with the antibody against tau. FIGS. 5B and 5D show the results of immunostaining with the antibody against Aβ. As a result of comparing the in vitro autoradiography image of the temporal lobe with the immunostaining images of tau and Aβ, the radioactivity accumulation onto the brain tissue section of the temporal lobe was consistent with the accumulation of tau as compared with the accumulation of Aβ, demonstrating that each compound of [$^{125}$I]BIP-NMe$_2$, [$^{125}$I]BIP-OMe, and [$^{125}$I]BIP-Me clearly visualizes tau accumulated in the brain with AD.

(Evaluation 2) Evaluation of In Vivo Radioactivity Distribution in Normal Mouse

Each compound of [$^{125}$I]BIP-NMe$_2$, [$^{125}$I]BIP-OMe, and [$^{125}$I]BIP-Me synthesized according to the method shown in Example 7 was diluted with saline containing 10 vol % ethanol and 0.1 vol % Tween 80. Each radioactive iodine-labeled BIP derivative compound was administered to a group of 5-week-old ddY male mice (26 to 28 g; each group involved 5 mice) from the tail veins thereof at 19.6 to 29.4 kBq (100 µL) per mouse. After 2, 10, 30, or 60 minutes, the mice were slaughtered. After blood collection, the organs were taken out, and their weights and radioactivity were measured.

The results are shown in Tables 2 to 4. In Tables 2 to 4, the numerical values shown in the column "Time after administration" are means of % ID for the stomach and the thyroid gland and means of % ID/g for the other tissues with standard deviation (SD) shown in parenthesis. Each compound of [$^{125}$I]BIP-NMe$_2$, [$^{125}$I]BIP-OMe, and [$^{125}$I]BIP-Me exhibited high transfer to the brain early after administration and then rapid clearance from the brain. Also, all of the BIP derivative compounds exhibited a behavior of being taken up into the kidney and the liver early after administration and then gradually excreted from the liver to the intestine. Furthermore, accumulation to the thyroid gland was relatively low, suggesting that marked deiodination does not occur in living body.

TABLE 2

| Tissue | Time after administration of [$^{125}$I]BIP-NMe$_2$ (min) | | | |
|---|---|---|---|---|
| | 2 | 10 | 30 | 60 |
| Blood | 2.91(0.75) | 1.48(0.18) | 1.18(0.26) | 0.93(0.23) |
| Liver | 9.78(2.50) | 18.1(0.53) | 12.7(1.35) | 5.82(0.91) |
| Kidney | 14.3(1.91) | 17.0(1.70) | 7.45(1.11) | 5.45(1.90) |
| Intestine | 3.07(0.52) | 7.45(0.50) | 14.5(3.43) | 23.5(3.65) |
| Spleen | 2.97(0.92) | 5.15(0.84) | 2.97(0.44) | 1.97(0.25) |
| Pancreas | 5.66(1.03) | 4.77(0.27) | 1.51(0.19) | 0.80(0.15) |
| Heart | 6.38(1.09) | 2.53(0.24) | 1.00(0.15) | 0.63(0.05) |
| Lung | 8.80(1.70) | 3.59(0.43) | 1.77(0.31) | 0.99(0.07) |
| Stomach | 1.71(0.43) | 3.30(0.49) | 6.35(1.13) | 7.59(1.39) |
| Brain | 3.98(0.32) | 1.66(0.16) | 0.38(0.03) | 0.16(0.01) |
| Thyroid gland | 0.05(0.03) | 0.03(0.01) | 0.02(0.01) | 0.01(0.00) |

TABLE 3

| Tissue | Time after administration of [125I]BIP-OMe (min) | | | |
|---|---|---|---|---|
| | 2 | 10 | 30 | 60 |
| Blood | 5.41(0.40) | 3.39(0.12) | 2.24(0.27) | 1.27(0.15) |
| Liver | 17.8(3.98) | 16.2(1.80) | 7.25(1.28) | 4.61(0.35) |
| Kidney | 8.66(0.73) | 7.38(1.46) | 5.74(2.30) | 2.20(1.20) |
| Intestine | 2.94(0.15) | 8.99(1.43) | 16.8(4.30) | 20.1(4.03) |
| Spleen | 3.60(1.10) | 3.16(0.18) | 1.07(0.08) | 0.63(0.10) |
| Pancreas | 4.38(0.30) | 1.59(0.18) | 0.86(0.22) | 0.53(0.13) |
| Heart | 5.17(0.27) | 1.94(0.18) | 0.99(0.08) | 0.52(0.08) |
| Lung | 6.09(0.34) | 3.33(0.24) | 1.76(0.11) | 1.21(0.30) |
| Stomach | 2.30(0.33) | 5.47(0.88) | 6.62(1.28) | 5.34(1.23) |
| Brain | 4.30(0.41) | 0.71(0.14) | 0.17(0.02) | 0.08(0.03) |
| Thyroid gland | 0.10(0.05) | 0.04(0.02) | 0.01(0.00) | 0.01(0.00) |

TABLE 4

| Tissue | Time after administration of [125I]BIP-Me (min) | | | |
|---|---|---|---|---|
| | 2 | 10 | 30 | 60 |
| Blood | 3.63(0.19) | 2.37(0.22) | 1.53(0.52) | 0.77(0.12) |
| Liver | 19.7(2.89) | 13.7(1.67) | 7.32(0.71) | 4.69(0.54) |
| Kidney | 7.32(0.61) | 6.75(0.83) | 4.05(1.19) | 2.19(1.23) |
| Intestine | 3.38(0.55) | 14.2(5.56) | 19.5(2.03) | 28.7(5.09) |
| Spleen | 4.22(0.43) | 1.94(0.29) | 0.60(0.13) | 0.36(0.10) |
| Pancreas | 3.85(0.39) | 1.38(0.29) | 0.50(0.08) | 0.40(0.24) |
| Heart | 4.40(0.59) | 1.61(0.19) | 0.66(0.10) | 0.36(0.07) |
| Lung | 6.54(0.76) | 2.37(0.31) | 1.14(0.11) | 0.65(0.11) |
| Stomach | 2.68(0.25) | 6.52(1.23) | 7.05(2.50) | 7.43(1.29) |
| Brain | 4.28(0.50) | 0.94(0.17) | 0.14(0.03) | 0.04(0.00) |
| Thyroid gland | 0.06(0.03) | 0.03(0.02) | 0.02(0.00) | 0.01(0.00) |

7-Tributylstannyl-3-aminopyrido[1,2-a]benzimidazole and 7-tributylstannyl-3-methylaminopyrido[1,2-a]benzimidazole are each synthesized according to the method shown in the scheme 1, and 7-[$^{125}$I]iodo-3-aminopyrido[1,2-a]benzimidazole and 7-[$^{125}$I]iodo-3-methylaminopyrido[1,2-a]benzimidazole are each obtained according to the method of Example 7.

7-Amino-3-tributylstannylpyrido[1,2-a]benzimidazole, 7-methylamino-3-tributylstannylpyrido[1,2-a]benzimidazole, 7-dimethylamino-3-tributylstannylpyrido[1,2-a]benzimidazole, 7-methoxy-3-tributylstannyl-pyrido[1,2-a]benzimidazole, and 7-methyl-3-tributylstannylbenzo[4,5]imidazo[1,2-a]pyridine are each synthesized according to the method shown in the scheme 2, and 7-amino-3-[$^{125}$I]iodopyrido[1,2-a]benzimidazole, 7-methylamino-3-[$^{125}$I]iodopyrido[1,2-a]benzimidazole, 7-dimethylamino-3-[$^{125}$I]iodopyrido[1,2-a]benzimidazole, 7-methoxy-3-[$^{125}$I]iodopyrido[1,2-a]benzimidazole, and 7-methyl-3-[$^{125}$I]iodobenzo[4,5]imidazo[1,2-a]pyridine are each obtained according to the method of Example 7.

In vitro autoradiography evaluation is conducted according to the method shown in Evaluation 1 using the obtained $^{125}$I-labeled compounds to confirm that they have binding selectivity for tau accumulated in the brain with AD. Also, in vivo radioactivity distribution evaluation in normal mice is conducted according to the method shown in Evaluation 2 using these $^{125}$I-labeled compounds to confirm transfer to the brain and subsequent clearance from the brain.

The results shown above indicate that the radioactive halogen-labeled compound according to the present invention can selectively and noninvasively image the tau protein in the brain.

This application claims the priority based on Japanese Patent Application No. 2015-161472 filed on Aug. 19, 2015, the disclosure of which is incorporated herein in its entirety.

The invention claimed is:

1. A radioactive iodine-labeled compound represented by the following formula (1) or a salt thereof:

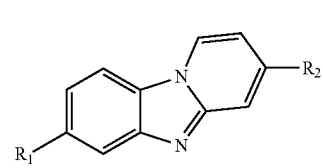

(1)

wherein one of $R_1$ and $R_2$ is a radioactive iodine atom, and the other is an amino group, an alkylamino group having 1 to 4 carbon atoms, or a dialkylamino group having 2 to 4 carbon atoms.

2. The radioactive iodine-labeled labeled compound or a salt thereof according to claim 1, wherein the radioactive iodine atom is $^{123}$I, $^{124}$I, $^{125}$I, or $^{131}$I.

3. The radioactive iodine-labeled compound or a salt thereof according to claim 1, wherein in the formula (1), $R_1$ is a radioactive iodine atom, and $R_2$ is a dialkylamino group having 2 to 4 carbon atoms.

4. A radiopharmaceutical comprising a radioactive iodine-labeled compound or a salt thereof according to claim 1.

5. The radiopharmaceutical according to claim 4, which is for use in single photon emission computed tomography (SPECT).

6. A diagnostic agent for Alzheimer's disease comprising a radioactive iodine-labeled compound or a salt thereof according to claim 1.

7. A compound represented by the following formula (2) or a salt thereof:

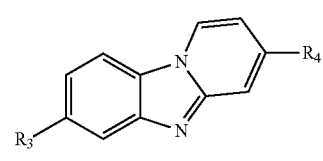

(2)

wherein one of $R_3$ and $R_4$ is, a trialkylstannyl group, or a trialkylsilyl group, and the other is an alkyl group having 1 to 4 carbon atoms, an alkoxy group having 1 to 4 carbon atoms, an amino group, an alkylamino group having 1 to 4 carbon atoms, or a dialkylamino group having 2 to 4 carbon atoms.

8. A method for producing a radioactive iodine-labeled compound comprising the step of subjecting a compound represented by the following formula (2) or a salt thereof under a radioactive iodination reaction to obtain the radioactive iodine-labeled compound represented by the following formula 1:

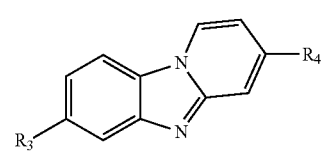

(2)

wherein one of $R_3$ and $R_4$ is, a trialkylstannyl group, or a trialkylsilyl group, and the other is an amino group, an alkylamino group having 1 to 4 carbon atoms, or a dialkylamino group having 2 to 4 carbon atoms, and
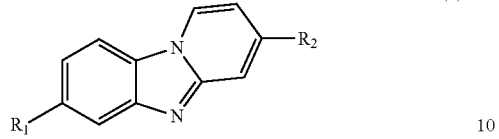
(1)
wherein one of $R_1$ and $R_2$ is a radioactive iodine atom, and the other is an amino group, an alkylamino group having 1 to 4 carbon atoms, or a dialkylamino group having 2 to 4 carbon atoms.
* * * * *